(12) United States Patent
Kamei et al.

(10) Patent No.: US 10,582,242 B2
(45) Date of Patent: Mar. 3, 2020

(54) SERVER APPARATUS AND METHOD OF TRANSMITTING VIDEO DATA

(71) Applicant: CANON KABUSHIKI KAISHA, Tokyo (JP)

(72) Inventors: Yoichi Kamei, Yokohama (JP); Shinichi Matsumoto, Yokohama (JP); Akihiro Kohno, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/289,029

(22) Filed: Oct. 7, 2016

(65) Prior Publication Data

US 2017/0026679 A1    Jan. 26, 2017

Related U.S. Application Data

(63) Continuation of application No. 13/273,591, filed on Oct. 14, 2011, now Pat. No. 9,491,416.

(30) Foreign Application Priority Data

| Oct. 16, 2010 | (JP) | 2010-233163 |
| Oct. 21, 2010 | (JP) | 2010-236679 |
| Oct. 28, 2010 | (JP) | 2010-242465 |

(51) Int. Cl.
| G06F 15/16 | (2006.01) |
| H04N 21/258 | (2011.01) |
| G06F 19/00 | (2018.01) |
| G06Q 50/24 | (2012.01) |
| G16H 10/60 | (2018.01) |

(Continued)

(52) U.S. Cl.
CPC ..... *H04N 21/25816* (2013.01); *G06F 19/321* (2013.01); *G06Q 50/24* (2013.01); *G16H 10/60* (2018.01); *H04N 5/23206* (2013.01); *H04N 5/23216* (2013.01); *H04N 7/185* (2013.01); *H04N 21/234* (2013.01); *H04N 21/6334* (2013.01)

(58) Field of Classification Search
None
See application file for complete search history.

(56) References Cited

U.S. PATENT DOCUMENTS

| 6,104,860 A | 8/2000 | Lee | |
| 2001/0024233 A1* | 9/2001 | Urisaka | H04N 5/232 348/211.6 |

(Continued)

FOREIGN PATENT DOCUMENTS

| CN | 1497937 A | 5/2004 |
| CN | 1574891 A | 2/2005 |

(Continued)

*Primary Examiner* — Padma Mundur
(74) *Attorney, Agent, or Firm* — Canon U.S.A., Inc. I.P. Division

(57) ABSTRACT

When a camera server receives an instruction involving invalidation of viewing limitation (masking processing) of video from a privileged client, the camera server limits viewing of video data with respect to a general client and a recording client. The camera server stores the video data of a limited period in a secondary storage device. When the camera server receives an instruction involving validation of the viewing limitation from the privileged client, the camera server transmits the stored video data of the limiting period to the recording client.

6 Claims, 6 Drawing Sheets

(51) Int. Cl.
*H04N 7/18* (2006.01)
*H04N 5/232* (2006.01)
*H04N 21/234* (2011.01)
*H04N 21/6334* (2011.01)

(56) References Cited

U.S. PATENT DOCUMENTS

| | | | |
|---|---|---|---|
| 2006/0002315 A1* | 1/2006 | Theurer | G06F 3/0481 |
| | | | 370/261 |
| 2006/0279253 A1 | 12/2006 | Kawai | |
| 2008/0055422 A1* | 3/2008 | Takayama | H04N 5/232 |
| | | | 348/211.8 |
| 2008/0117295 A1 | 5/2008 | Ebrahimi | |
| 2008/0144883 A1* | 6/2008 | Kacker | H04N 1/00838 |
| | | | 382/100 |
| 2012/0046972 A1* | 2/2012 | Tonti | G06F 19/321 |
| | | | 705/3 |

FOREIGN PATENT DOCUMENTS

| | | |
|---|---|---|
| CN | 101133651 A | 2/2008 |
| JP | 03880495 B2 | 2/2007 |

* cited by examiner

SERVER APPARATUS AND METHOD OF TRANSMITTING VIDEO DATA

CROSS REFERENCE TO RELATED APPLICATIONS

This application is a Continuation of U.S. patent application Ser. No. 13/273,591 filed Oct. 14, 2011, which claims the benefit of Japanese Patent Applications No. 2010-233163 filed Oct. 16, 2010, No. 2010-236679 filed Oct. 21, 2010, and No. 2010-242465 filed Oct. 28, 2010, all of which are hereby incorporated by reference herein in their entireties.

BACKGROUND OF THE INVENTION

Field of the Invention

The present invention relates to a video distribution system for distributing video data according to an authority of a client.

Description of the Related Art

Recently, a camera compatible with network has come to be widely used in various usages for the purposes of, for example, security and investigation used in, for example, residential districts, shops, banks, and stations. In order to avoid an invasion of privacy such as leakage of private information and confidential information in a photographic area, a camera capable of setting a privacy masking area in the photographic area for the sake of a viewing limitation is showing up in the market.

Conventionally, for example, Japanese Patent application Laid-open No. 2001-69494 discusses a technique that masking data for masking a privacy zone of which an image is displayed is stored to provide masking to a portion of the image according to the masking data.

However, continuity of video data received by a client who has no viewing authority with respect to the area with viewing limitation may be degraded depending on an instruction from a client having the viewing authority of the area with the viewing limitation.

A case that the area with the viewing limitation is a privacy masking area (hereinafter referred to as a masking area) is exemplified below. In this case, when the masking area is being set (moved or changed in size) by a client having the viewing authority, if video data is not distributed to a client who has no viewing authority, the continuity of the video data received by the client having no viewing authority may be degraded.

Also, a case that the area with the viewing limitation is an area outside a limited range of a panning angle and a tilting angle of the camera is exemplified below. In this case, when a client having the viewing authority is controlling the panning angle or the tilting angle beyond the limited range, if the video data is not distributed to a client having no viewing authority, continuity of the video data received by the client having no viewing authority may be degraded.

SUMMARY OF THE INVENTION

The present invention is directed to a server apparatus capable of alleviating degradation of continuity of video data received by a client having no viewing authority with respect to an area with a viewing limitation.

According to an aspect of the present invention, a server apparatus for transmitting video data to a client includes a receiving unit configured to receive an instruction involving invalidation of a viewing limitation of video based on the video data from a client having a viewing authority of an area with the viewing limitation, a transmission unit configured to limit viewing of the video data with respect to a client having no viewing authority of the area with the viewing limitation in response to reception of the instruction involving the invalidation of the viewing limitation, and a storage unit configured to store video data of a limiting period during which viewing of the video data is limited with respect to the client having no viewing authority, wherein the transmission unit transmits the video data of the limiting period to the client having no viewing authority in response to reception, by the receiving unit, of an instruction involving validation of the invalidated viewing limitation.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
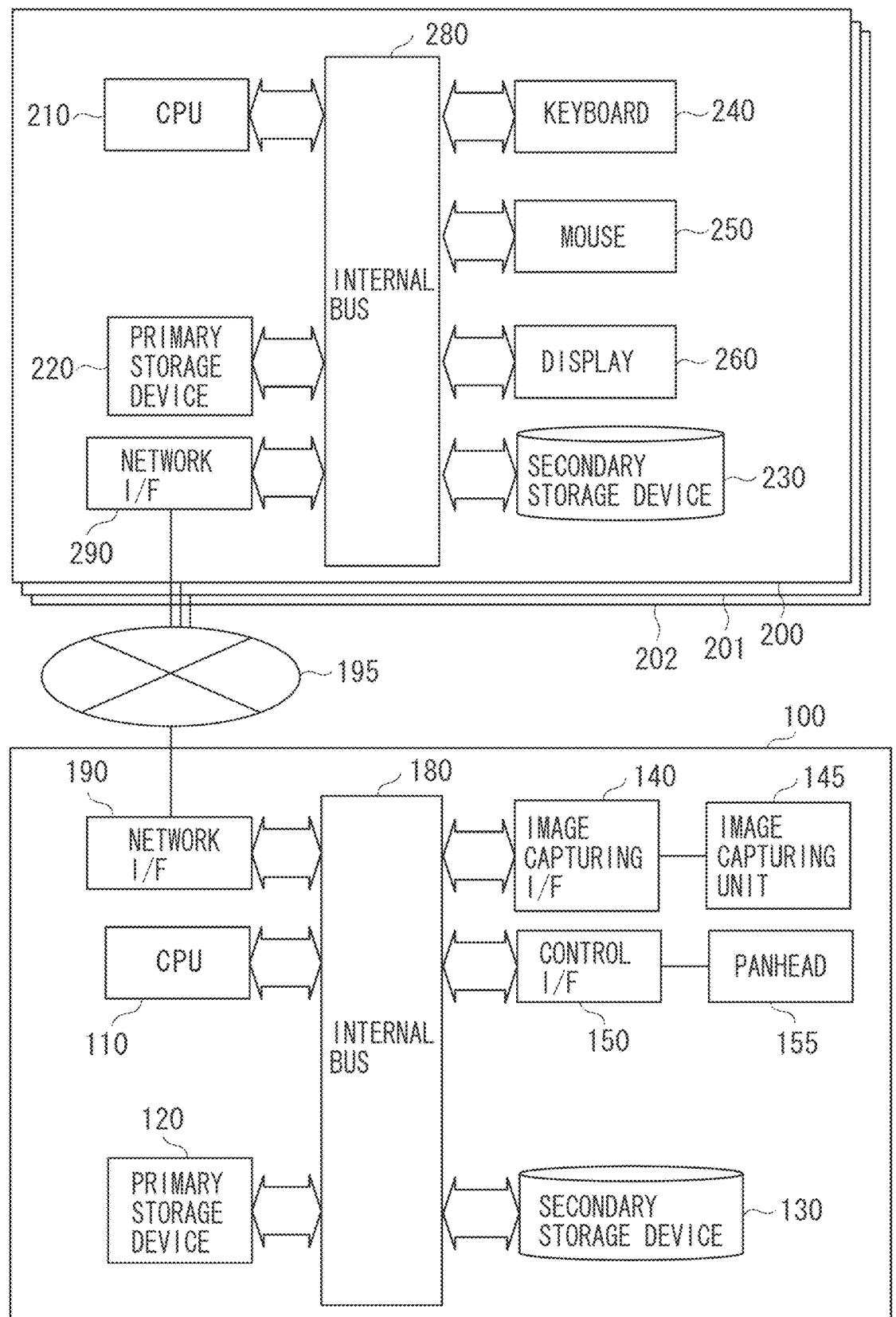
FIG. 1 is a block diagram illustrating configurations of a camera server and a client according to an exemplary embodiment of the present invention.
Figure 5:
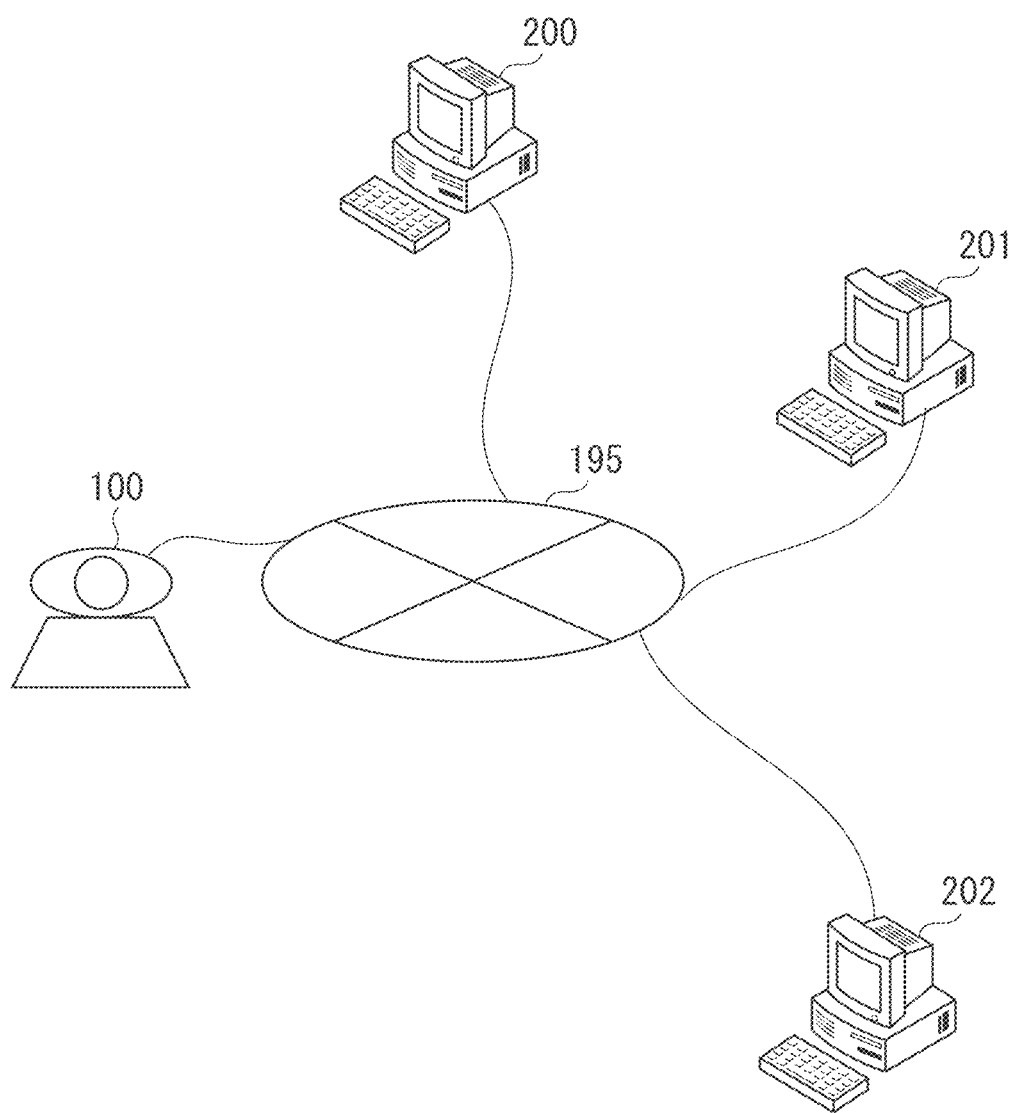
FIG. 5 illustrates an example of a system configuration according to an exemplary embodiment of the present invention.

FIG. 1 is a block diagram illustrating configurations of a camera server 100 and a client 200 according to an exemplary embodiment of the present invention. As illustrated in FIG. 1, the camera server 100 is connected to a plurality of clients (200, 201, and 202) via a network 195. In the present exemplary embodiment, the camera server 100 is connected to a privileged client 200, a general client 201, and a recording client 202. The privileged client 200 has a viewing authority of an area with a viewing limitation (e.g., a privacy masking area). On the other hand, the general client 201 and the recording client 202 have no viewing authority of the area with the viewing limitation. The general client 201 displays video data received from the camera server 100. The recording client 202 records video data received from the camera server 100. However, a type of client and the number of clients are not limited to the above examples. An example of connection between the camera server 100 and each of the clients 200, 201, and 202 is illustrated in FIG. 5.

In the present exemplary embodiment, a case that the viewing limitation is the one set according to privacy masking processing (hereinafter referred to as masking processing) is mainly described below. In this case, the area with the viewing limitation means a privacy masking area (hereinafter referred to as a masking area). The privileged client 200 of the present exemplary embodiment can add, delete, move, and change-in-size the masking area by using a below-described setting tool.

The viewing limitation is not limited to the masking processing. The viewing limitation can also be, for example, a range limitation in an imaging direction (e.g., range limitation of an operable panning angle, tilting angle, and/or rotation angle), prohibition against operation in the imaging direction, and prohibition against operation in imaging direction except for a preset value. The above settings are mere examples of setting contents. The contents that can be set by using the setting tool are not limited to the above-described setting contents. For example, in a case where the camera server 100 has a function of detecting a change of captured video, a position and a size of a detecting area for detecting the change thereof and settings of detecting conditions or the like can be performed by the setting tool. Also, not all the above-described setting contents are necessary to be set by the setting tool.

The camera server 100 includes a central processing unit (CPU) 110, a primary storage device 120, a secondary storage device 130, an image capturing interface (I/F) 140, a control I/F 150, and a network I/F 190. The image capturing I/F 140 of the camera server 100 is connected to an image capturing unit 145. The control I/F 150 of the camera server 100 is connected to a panhead 155.

The primary storage device 120 is a writable high-speed storage device as typified by a random access memory (RAM). An operating system (OS), various programs, and different types of data are loaded to the primary storage device 120. The primary storage device 120 is also used as a work area of the OS and the various programs. A primary storage device 220 of each of the clients 200, 201, and 202 has the same configuration.

The secondary storage device 130 is a nonvolatile storage device as typified by a floppy disk drive (FDD), a hard disk drive (HDD), a flash memory, a compact disc read-only memory (CD-ROM) drive or the like. The secondary storage device 130 is also used as a permanent storage area for the OS, the various programs, and the different types of data. The secondary storage device 130 is also used as a short-term storage area for the different types of data. The secondary storage device 130 is also used as a storage region storing video data. A secondary storage device 230 of each of the clients 200, 201, and 202 has the same configuration.

The image capturing I/F 140 is connected to the image capturing unit 145 to transfer the video data captured by the image capturing unit 145 to the primary storage device 120 after converting/compressing the video data into a predetermined format.

The control I/F 150 is connected to the panhead 155 in order to obtain states of a pan mechanism, a tilt mechanism, and a rotation mechanism of the panhead 155 and to control the panhead 155 according to an instruction from each client 200, 201, or 202. The panhead 155 is provided with the image capturing unit 145 to be mounted thereon. The imaging direction of the image capturing unit 145 is controlled under the control of the pan mechanism, the tilt mechanism, and the rotation mechanism of the panhead 155.

The network I/F 190 is connected to the network 195 to establish a communication with each client 200, 201, or 202 via a communication medium, e.g., the Ethernet.

The network 195 includes a plurality of routers, switches, cables, and the like which satisfy a communication standard such as the Ethernet. As far as a communication can be established between the server and each client without a problem, any communication standard, scale, or configuration can be employed for the network 195 in the present exemplary embodiment. Therefore, the network 195 is applicable to the Internet and a local area network (LAN).

Each client 200, 201, or 202 includes a CPU 210, a primary storage device 220, a secondary storage device 230, a keyboard 240, a mouse 250, a display 260, and a network I/F 290, which are connected with each other via an internal bus 280.

The keyboard 240 and the mouth 250 are typical input device for issuing an instruction. The display 260 is a display screen for displaying video according to video data distributed from the camera server 100. The secondary storage device 230 is also used as a recording area of the distributed video.

Figure 2:
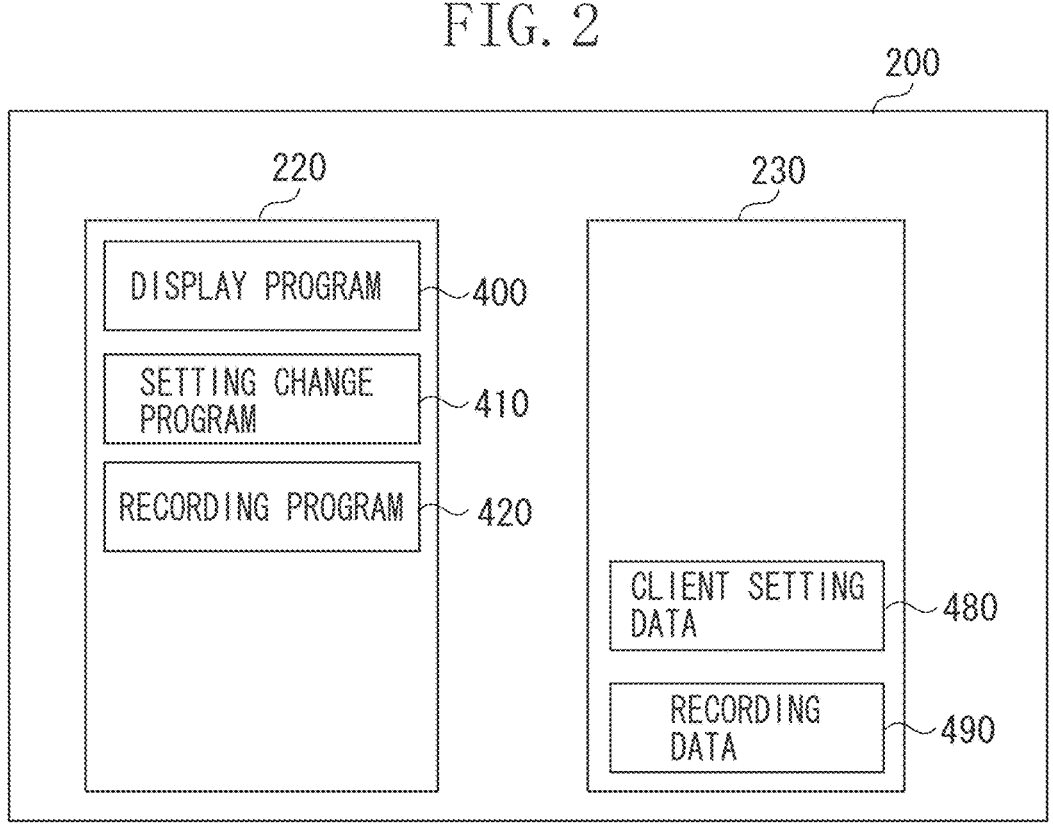
FIG. 2 schematically illustrates programs and data retained by the camera server and the client.
Figure 2:
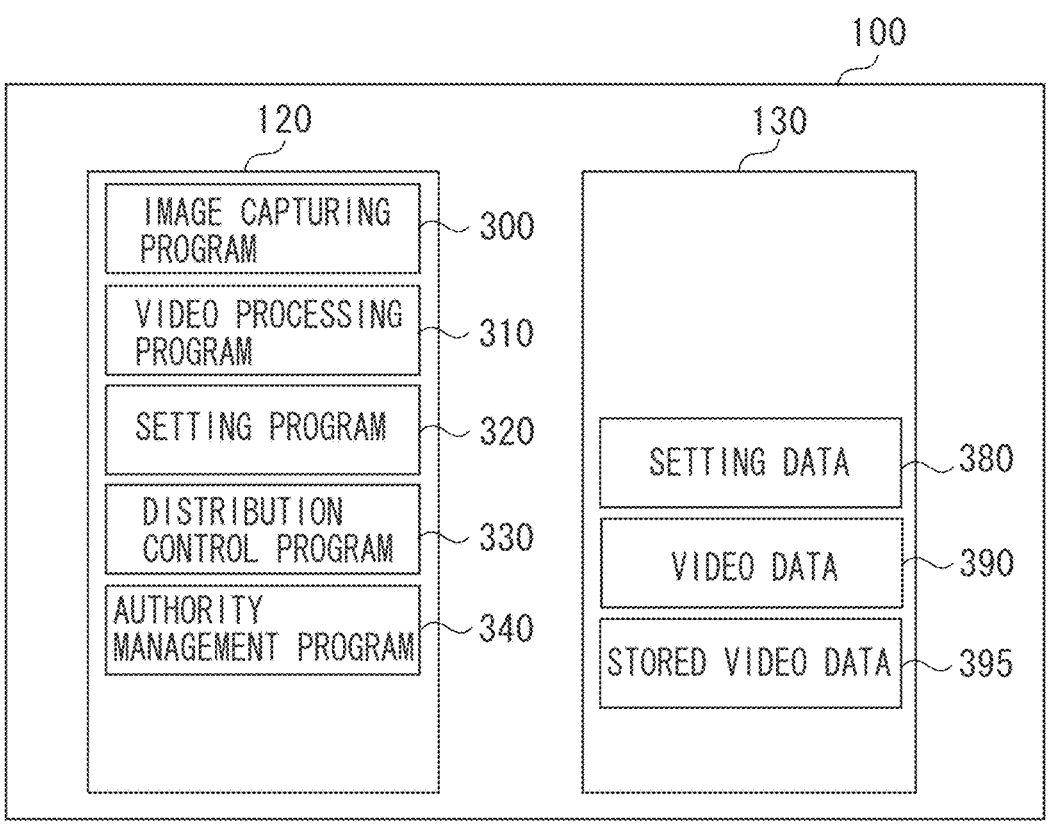

FIG. 2 schematically illustrates programs and data stored in the primary storage device 120 and the secondary storage device 130 of the camera server 100 and programs and data stored in the primary storage device 220 and the secondary storage device 230 of each client 200, 201, or 202.

As illustrated in FIG. 2, an image capturing program 300, a video processing program 310, a setting program 320, a distribution control program 330, and an authority management program. 340 are loaded to the primary storage device 120 of the camera server 100.

Setting data 380, video data 390, and stored video data 395 are stored in the secondary storage device 130 of the camera server 100.

A display program 400, a setting change program 410, and a recording program 420 are loaded to the primary storage device 220 of the privileged client 200.

Client setting data 480 and recording data 490 are stored in the secondary storage device 230 of the privileged client 200.

At least the display program 400 is loaded to the primary storage device 220 of the general client 201. At least the recording program 420 is loaded to the primary storage device 220 of the recording client 202. Each program loaded to the primary storage device 120 of the camera server 100 of the present exemplary embodiment is stored in the secondary storage device 130 of the camera server 100. Similarly, each program to be loaded to the primary storage device 220 of each client 200, 201, or 202 is stored in the secondary storage device 230 of each client 200, 201, or 202.

Now, descriptions are made as to the image capturing program 300, the video processing program 310, the setting program 320, the distribution control program 330, and the authority management program 340 of the camera server 100. The above-described programs are read out by the CPU 110 from the secondary storage device 130 to the primary storage device 120 to be executed thereon.

The image capturing program 300 causes the secondary storage device 130 to store the video data 390 acquired by capturing processing performed by the image capturing unit 145.

In the present exemplary embodiment, the video data 390 is stored in the secondary storage device 130; however, it also may be stored in a high-speed storage device such as the primary storage device 120 or a buffer. The image capturing program 300 controls the panhead 155 via the control I/F 150 according to, for example, control signals from the clients 200, 201, and 202.

The video processing program 310 sets the viewing limitation (e.g., masking processing), as required, with respect to the video data 390 acquired by the capturing processing performed by the image capturing unit 145.

The setting program 320 changes the setting data 380 of the secondary storage device 130 in response to a change according to an instruction from each client 200, 201, or 202 or an instruction from the distribution control program.

The distribution control program 330 controls other programs in response to the instruction from each client 200, 201, or 202. A detailed description of the distribution control program is described below with reference to FIG. 3.

The authority management program 340 makes a response as to information on presence or absence of an accessing right of the client or whether the client has the viewing authority of an area with the viewing limitation according to an inquiry from the distribution control program 330.

Now, descriptions are made as to the display program 400, the setting change program 410, and the recording program 420 of the privileged client 200. At least the display program 400 is loaded to the general client 201. At least the recording program 420 is loaded to the recording client 202.

The display program 400 makes a request for distributing the video data 390 to the camera server 100 and displays the video data 390 acquired from the camera server 100 on the display 260.

The setting change program 410 makes a setting request to the camera server 100 according to an instruction of a general inputting device such as the keyboard 240 or the mouse 250 of the privileged client 200. According to the setting request, for example, a position and/or a size of the masking area can be changed. The setting change program is installed on the privileged client 200 having a privilege and is activated by the below-described setting tool.

The recording program 420 makes a distribution request of the video data 390 to the camera server 100 and causes the secondary storage device 230 to store the video data 390 from the camera server 100. According to the recording program 420, in a case where video data 390 lacks a portion of a period, the recording program 420 makes the distribution request of the stored video data 395 to the camera server 100, and the stored video data 395 from the camera server 100 is stored in the secondary storage device 230. The recording program 420 is described below in detail with reference to FIG. 4.

Each of the above-described programs can concurrently execute processing. More specifically, for example, the position and the size of the masking area can be changed while the video data 390 is displayed.

Figure 3:
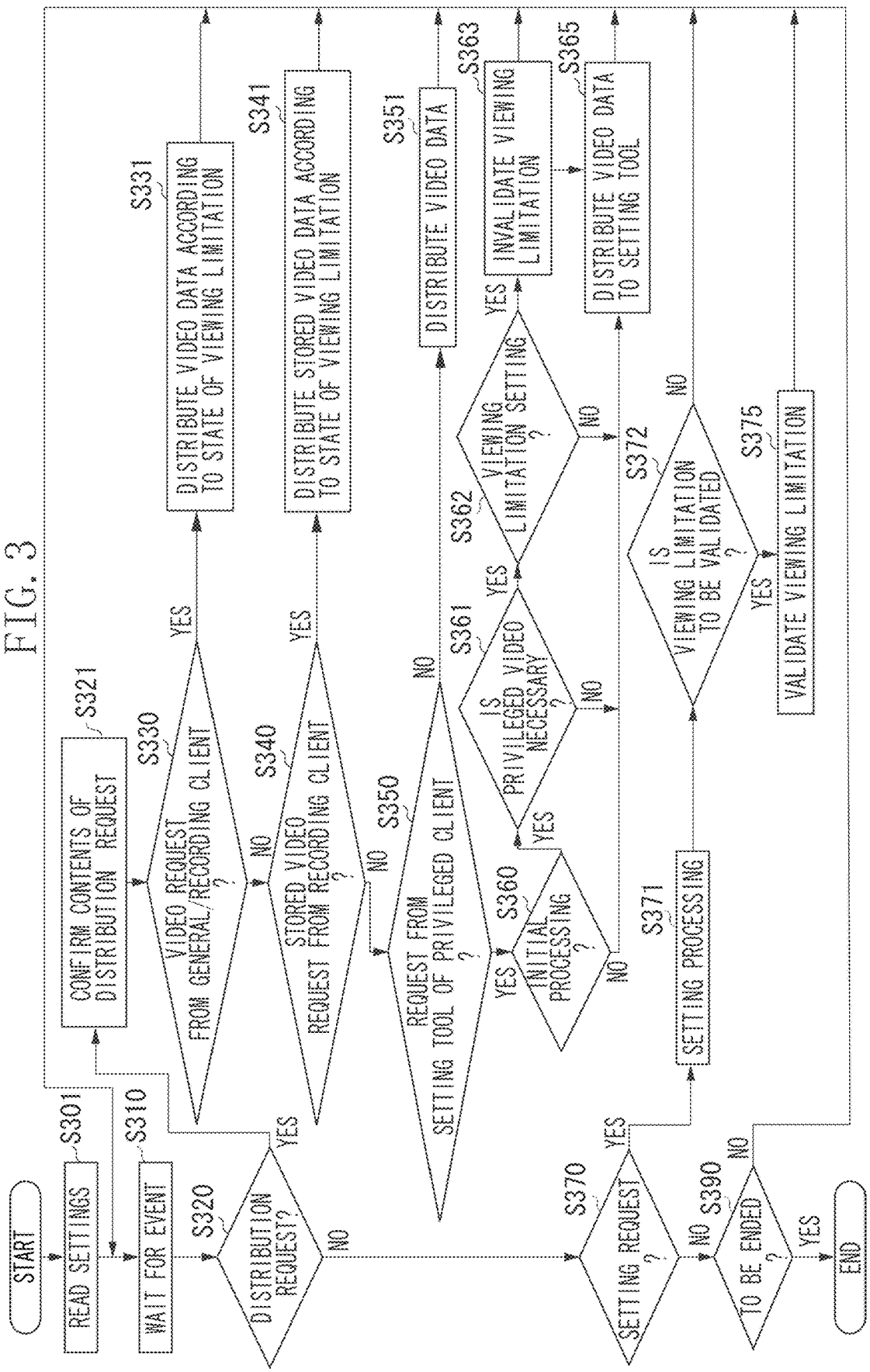
FIG. 3 is a flow chart illustrating processing performed by the camera server.

Now, processing by the camera server 100 of the present exemplary embodiment is described below with reference to FIG. 3. The camera server 100 distributes the video data to the clients. In the camera server 100, processing illustrated in the flow chart of FIG. 3 can be realized such that the CPU 110 reads one of the programs stored in the secondary storage device 130 to the primary storage device 120 to execute the program thereon. The CPU 110 can realize the following processing such that the CPU 110 reads out and executes the image capturing program 300, the video processing program 310, the setting program 320, the distribution control program 330, and the authority management program 340.

In step S301, the CPU 110 of the camera server 100 reads the setting data 380 stored in the secondary storage device 130. The setting data 380 includes information on, for example, a position of the masking area. The setting data 380 may include information on a range limitation of, for example, the panning angle, the tilting angle, the rotation angle, and a zooming value, or information on an operation prohibition of, for example, a pan control, a tilt control, a rotation control, and a zoom control. Further, the setting data 380 may be a setting value regarding a preset value of, for example, the panning angle, the tilting angle, the rotation angle, and the zooming value. Still further, the setting data 380 includes information indicating whether the viewing limitation (e.g., masking processing) is presently valid.

When the CPU 110 has completed reading the setting data 380, then in step S310, the CPU 110 waits for an event. The camera server 100 of the present exemplary embodiment determines that the event has occurred in a case where the camera server 100 receives a distribution request of the video data 390 and the stored video data 395 from clients 200, 201, or 202 or in a case where the camera server 100 receives a setting request of the setting data 380 from the privileged client 200.

In step S320, when an event is detected, the camera server 100 determines whether the event is a reception of the distribution request from the client 200, 201, or 202. When the camera server 100 determines that the event is the reception of the distribution request (YES in step S320), then in step S321, the CPU 110 confirms contents of the received distribution request. The distribution request includes the distribution request of the video data 390 from the general client 201 and the distribution request of the video data 390 or the stored video data 395 from the recording client 202. Further, the distribution request includes the distribution request of the video data 390 from the privileged client 200 and the distribution request of the video data 390 from the setting tool of the privileged client 200.

In a case where the CPU 110 of the camera server 100 determines that the event is the distribution request of the video data 390 from the general client 201 or the recording client 202 (YES in step S330), then in step S331, the CPU 110 distributes the video data 390 according to a state of the viewing limitation. In other words, when the camera server 100 receives the distribution request of the video data 390 from the general client 201 while the viewing limitation (e.g., masking processing) is valid, the camera server 100 distributes the video data 390. On the other hand, the camera server 100 does not distribute the video data 390 even when the camera server 100 receives the distribution request of the video data 390 from the general client 201 or the recording client 202 while the viewing limitation is not valid. When the camera server 100 of the present exemplary embodiment receives the distribution request of the video data 390 from the general client 201 or the recording client 202 while the viewing limitation is invalid, the camera server 100 notifies that the distribution of the video data 390 is suspended. As described below, the viewing limitation is set to be invalid while the setting tool is changing the position and the size of the masking area.

In a case where the CPU 110 of the camera server 100 determines that the event is the reception of the distribution request of the stored video data 395 from the recording client 202 (YES in step S340), then in step S341, the CPU 110 distributes the stored video data 395 according to the state of the viewing limitation. More specifically, in a case where the camera server 100 receives the distribution request of the stored video data 395 from the recording client 202 while the viewing limitation (e.g., masking processing) is valid, the camera server 100 distributes undistributed stored video data 395 to the recording client 202. The camera server 100 of the present exemplary embodiment distributes the stored video data 395 with the viewing limitation (i.e., having been subjected to the masking processing) to the recording client 202. The masking area at the moment is the one according to the setting at the time of the distribution of the stored video data 395. In a case where, for example, the range limitation of the panning angle or the tilting angle is set to the viewing limitation, the camera server 100 of the present exemplary embodiment does not distribute the stored video data 395 of a period that image capturing is performed with respect to the outside of the limited range to the recording client 202 even when it receives the distribution request of the stored video data 395. The camera server 100, however, can distribute the stored video data 395 without the viewing limitation according to an authority level of the recording client 202.

In a case where the camera server 100 determines that the event is not the reception of the distribution request of the video data 390 from the setting tool of the privileged client 200 (NO in step S350), then in step S351, the camera server 100 distributes the video data 390 to the privileged client 200. In the case of NO in step S350, the camera server 100 determines that the event is the distribution request of the video data 390 from the display program 400 of the privileged client 200. In a case where the event is the distribution request from the privileged client 200 but the request does not involve a setting change with respect to the camera server 100, the camera server 100 distributes the video data 390 according to a viewing authority of the privileged client 200.

On the other hand, in a case where the camera server 100 determines that the event is the reception of the distribution request of the video data 390 from the setting tool of the privileged client 200 (YES in step S350), then in step S360, the camera server 100 determines whether the distribution request is an initial distribution request after the setting processing of the below-described step S371 is performed. In a case where the camera server 100 determines that the event is the initial distribution request (YES in step S360), then in step S361, the camera server 100 determines whether video data without the viewing limitation (i.e., privileged video data) is to be distributed to the privileged client 200 who is a sender of the distribution request. A case where the privileged video data is essential is a case where contents of the setting set by the setting tool include a setting of the viewing limitation. In a case where the contents of the setting set by the setting tool include, for example, the setting of the privacy mask, the range limitation in the imaging direction, the operation prohibition in the imaging direction, and the operation prohibition with a value other than the preset value in the imaging direction, the camera server 100 determines that the distribution of the privileged video data is essential.

On the other hand, a case that the privileged video data is not essential is a case that the contents of the setting set by the setting tool do not include the setting of the viewing limitation. For example, in a case where the camera server 100 has a function of detecting a change of the captured video and in a case where the setting tool performs settings of the position and the size of the detecting area for detecting the change and a setting of detecting conditions, the camera server 100 determines that the distribution of the privileged video data is not essential.

In a case where the camera server 100 determines that the distribution of the privileged video data is essential (YES in step S361), then in step S362, the camera server 100 determines whether the setting of the viewing limitation (e.g., masking processing) is valid. In a case where the contents of the setting set by the setting tool include the setting of the viewing limitation (YES in step S361) and in a case where the setting of the viewing limitation is not presently valid, in step S362, the processing proceeds to NO. In a case where the camera server 100 determines that the setting of the viewing limitation is valid (YES in step S362), then in step S363, the viewing limitation is set to be invalid. In step S365, the camera server 100 distributes the video data to the setting tool of the privileged client 200.

In the present exemplary embodiment, in a case where the camera server 100 receives the distribution request of the video data 390 from the setting tool for the purpose of changing the position and the size of the masking area when the masking processing is valid, in step S362, the camera server 100 determines the processing as YES. In step S365, the CPU 110 of the camera server 100 distributes the privileged video data before being subjected to the masking processing to the privileged client 200. More specifically, in step S362 (i.e., receiving step), the camera server 100 receives an instruction involving invalidation of the viewing limitation of the video based on the video data 390 (e.g., masking processing) from the client (i.e., privileged client 200) having the viewing authority of the area with the viewing limitation.

In a case where a privileged video is not essential (NO in step S361), then in step S365, the camera server 100 distributes the video data to the setting tool.

In a case where the camera server 100 determines that the distribution request is a distribution request subsequent to the initial distribution request requested by the privileged client 200 (NO in step S360), since the viewing limitation has already been set to be invalid in step S363 in response to the initial distribution request, the processing of step S363 is skipped and the processing proceeds to step S365.

In a case where the setting of the viewing limitation is invalid (NO in step S362), since the processing of step S363 is not essential, the processing proceeds to step S365 to distribute the video to the setting tool.

The CPU 110 invalidates the viewing limitation in step S363 to suspend the distribution of the video data 390 to the other general client 201 and the recording client 202. The CPU 110 stores the video data 390 of a period that the distribution thereof is suspended in the secondary storage device 130 as the stored video data 395. In step S363 (i.e., transmission step), the CPU 110 of the camera server 100 suspends the distribution of the video data 390 to the client having no viewing authority of the area with the viewing limitation according to the reception of the instruction involving the invalidation of the viewing limitation. The CPU 110 of the camera server 100 notifies the general client 201 and the recording client 202 to the extent that the CPU 110 receives the instruction involving the invalidation of the viewing limitation from the privileged client 200.

The CPU 110 of the camera server 100 may output a predetermined image as a substitute image to the general client 201 after suspending the distribution of the captured image to the general client 201. Examples of the predetermined image may include an image that is preliminary stored in the secondary storage device 130 and represents that the camera server 100 is "in setting" and the captured image captured immediately before the distribution suspension processing is performed. The transmission of the predetermined image ends concurrently with an end of the distribution suspension processing. In the case of transmitting the substitute image, the CPU 110 of the camera server 100 transmits information on a period that the substitute image is transmitted to the general client 201. A type of the information on the period that the substitute image is transmitted is not specified but, for example, the information may be a time of a start of the transmission of the substitute image and a time of an end of the transmission of the substitute image. Transmission of the above information enables the general client 201 to determine the period that the substitute image is transmitted instead of the video data 390.

Alternatively, in a case where the CPU 110 of the camera server 100 receives the instruction involving the invalidation of the viewing limitation, the CPU 110 may distributes the video data provided that the viewing of the video data of which viewing limitation is invalidated is limited to the general client 201. For example, in a case where the CPU 110 of the camera server 100 receives the instruction involving the invalidation of the viewing limitation, the CPU 110 of the camera server 100 may transmit the video data of which viewing limitation is invalidated to the privileged client 200, whereas may transmit the video data still with the viewing limitation to the general client 201. In a case where the range limitation is set in the imaging direction with respect to the general client 201, if the instruction of photographing an area within the range limitation is made by the privileged client 200, the CPU 110 of the camera server 100 may limit the viewing of the limited range by superimposing the masking image over the video data. As described above, in a case where different types of video data are transmitted to the privileged client 200 and the general client 201, respectively, the CPU 110 of the camera server 100 transmits information on a period during which the video different from that distributed to the privileged client 200 is distributed to the general client 201. A type of information on the period is not specified. By the transmission of the above-described information, the general client 201 can determine the period during which the video different from that transmitted to the privileged client 200 is transmitted.

In view of the above, when the privileged client 200 makes the distribution request for the purpose of changing the setting of the contents to be limited, the CPU 110 of the camera server 100 can distribute the video in which the limitation is not imposed on the captured image according to the video processing to the privileged client 200. On the other hand, the CPU 110 of the camera server 100 can perform control to distribute the video to which the limitation is imposed according to the video processing to the general client 201. As described above, the processing for distributing different videos to the privileged client 200 and the general client 201, respectively, is ended at the time at which the viewing limitation is validated in step S375.

The CPU 110 of the camera server 100 limits the viewing of the video data to the client who does not have the viewing authority of the area with the viewing limitation in response to the reception of the instruction involving the invalidation of the viewing limitation. In a mode of the limitation, the CPU 110 can suspend the distribution of the video data to the general client 201. Alternatively, the CPU 110 can distribute the video data of which viewing limitation is invalidated to the privileged client 200, whereas can transmit the video data of which viewing limitation is still valid to the general client 201.

Accordingly, the image on which a masking image is not superimposed can be prevented from being unintentionally distributed to the general client 201 while the privileged client 200 is setting the mask setting.

The CPU 110 stores the video data of the period after the viewing limitation is invalidated in step S363 and before the viewing limitation is validated in the following step S375 (i.e., limited period) in the secondary storage device 130 in the form of the stored video data 395 (i.e., storage step).

On the other hand, in a case where the CPU 110 determines that the event is not the reception of the distribution request of the video data 390 or the stored video data 395 (NO in step S320), then in step S370, the CPU 110 determines whether the event detected in step S310 is the reception of the setting request for changing settings. In a case where the CPU 110 determines that the event is the reception of the setting request (YES in step S370), then in step S371, the CPU 110 changes the setting data 380, and, in step S372, determines whether the setting of the viewing limitation is changed from invalid to valid. For example, when the position of the masking area is changed by the setting tool and the OK button is pressed (YES in step S372), the privileged client 200 transmits the setting request thereof to the camera server 100 to notify a new position of the masking area. The camera server 100 changes the setting data 380 relating to the position of the masking area according to the setting request and changes the setting of the viewing limitation (i.e., masking processing) from invalid to valid. More specifically, in step S375, the CPU 110 receives the instruction (i.e., setting request) for validating the invalidated viewing limitation (i.e., masking processing).

In a case where the CPU 110 determines that the event is not the reception of the setting request (NO in step S370), then in step S390, the CPU 110 determines whether the distribution processing of the video data is to be ended. In a case where the CPU 110 determines that the distribution processing of the video data is to be ended (YES in step S390), the processing is ended.

In the present exemplary embodiment, a case that the viewing limitation is the masking processing, the area with the viewing limitation is the masking area, and the instruction involving the invalidation of the viewing limitation is the distribution request of the video data from the setting tool for changing the position and the size of the masking area is mainly exemplified. However, the present invention is not limited to the above-described example.

For example, the viewing limitation can be set to the range limitation of at least any one of the panning angle, the tilting angle, the rotation angle, and the zoom value of the imaging apparatus (i.e., image capturing unit 145). In this case, the area with the viewing limitation is an imaging region beyond a limited range. The user of the privileged client 200 transmits the distribution request of the video data from the setting tool to invalidate the viewing limitation, for example, when changing the limited range, thereby freely determining a new limited range in view of the video. During the above processing, suspension of the distribution of the video data to the general client 201 and the recording client 202 enables protection of privacy The viewing limitation can be set to an operation limitation of at least anyone of a panning operation, a tilting operation, a rotation operation, and a zooming operation with respect to the imaging apparatus (i.e., image capturing unit 145). In this case, the area with the viewing limitation is an imaging region other than the present panning angle, tilting angle, rotation angle, and zooming value. The user of the privileged client 200 temporarily invalidates the operation limitation according to the distribution request of the video data via the setting tool, thereby allowing the privileged client 200 to freely view the video. During the above processing, suspension of the distribution of the video data to the general client 201 and the recording client 202 enables the protection of privacy.

The viewing limitation can be set to operations of the panning angle and the tilting angle other than the preset value with respect to the imaging apparatus (i.e., image capturing unit 145). In this case, the area with the viewing limitation is the imaging region of the panning angle and the tilting angle other than the preset value. When, for example, the user of the privileged client 200 changes the preset value having been set, the user transmits the distribution request of the video data from the setting tool to invalidate the viewing limitation, thereby capable of freely viewing the video.

In the above-described exemplary embodiment, an example that the viewing limitation is invalidated according to the distribution request of the video data from the setting tool is described. However, for example, the viewing limitation of the camera server 100 can be invalidated according to a generation request of a panoramic image from the privileged client 200. More specifically, the viewing limitation can be the masking processing, the area with the viewing limitation can be the masking area, and the instruction involving the invalidation of the viewing limitation can be the generation request of a panoramic image. In a case where a plurality of pieces of video data that the privileged client 200 acquired from the camera server 100 are combined according to a projective transformation to generate a panoramic image, the privileged client 200 transmits the generation request of a panoramic image to the camera server 100 via the setting tool. The camera server 100 after receiving the generation request of a panoramic image invalidates the masking processing and transmits the video data before being subjected to the masking processing to the privileged client 200. As described above, the privileged client 200 combines the plurality of pieces of video data before being subjected to the masking processing by the projective transformation, thereby capable of generating the panoramic image. By generating the panoramic image from the video before being subjected to the masking processing and subjecting the panoramic image to the masking processing, quality of the panoramic image can be improved more than a case that the video data after being subjected to the masking processing is combined by the projective transformation to generate the panoramic image.

Figure 6:
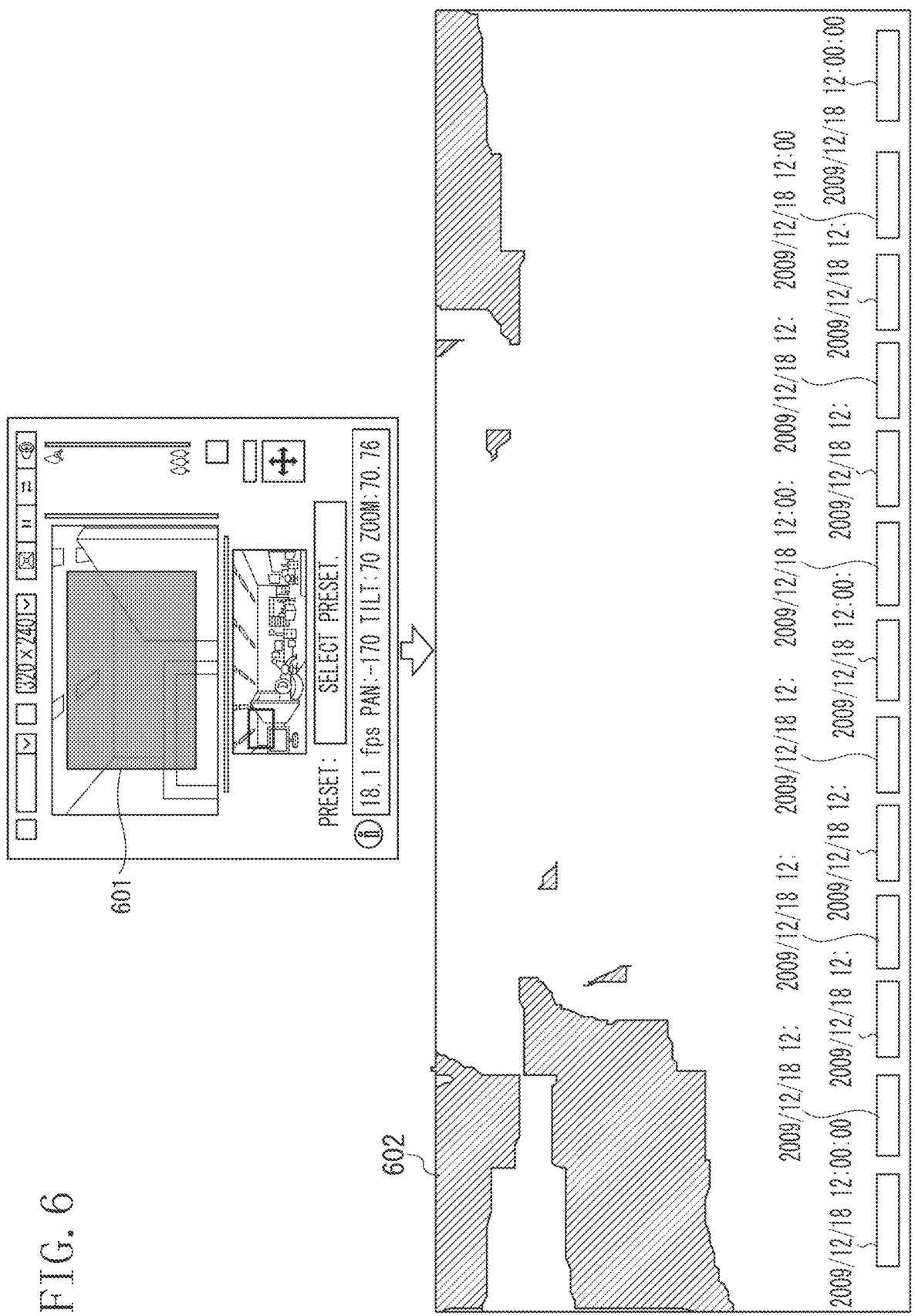
FIG. 6 illustrates an example of a panoramic image generated from video data superimposed with a privacy mask.

In other words, in a case where the plurality of pieces of video data after being subjected to the masking processing are further subjected to the projective transformation to generate the panoramic image based on the setting of the masking area, as illustrated in FIG. 6, the masking area may be deformed or the masking area may be moved to an unintended position. Therefore, the camera server 100 invalidates the masking processing in response to the reception of the generation request of the panoramic image from the privileged client 200. The camera server 100 distributes the video data before being subjected to the masking processing to the privileged client 200, and suspends the distribution of the video data to the general client 201 and the recording client 202 who have no viewing authorities of the masking area. The camera server 100 distributes the panoramic image, generated by the privileged client 200 and having been subjected to the masking processing, to the general client 201 and the recording client 202. Accordingly, a high-quality panoramic image can be generated and the privacy of the video can be protected. The masking processing may be performed by the privileged client 200 or by the camera server 100. In this case, also, instead of suspending the distribution of the video data to the general client 201, the video data of which viewing limitation is invalidated is transmitted to the privileged client 200 and the video data still with the viewing limitation may be transmitted to the general client 201.

The camera server 100 of the present exemplary embodiment transmits "keep alive" while the distribution of the video data to the general client 201 and the recoding client 202 is suspended. Accordingly, in the general client 201 and the recording client 202 to whom the distribution of the video data is suspended, the communication can be set so as not to be cut. The camera server 100 of the present exemplary embodiment can start the processing of the viewing limitation based on the setting set in step S371 without waiting for the reception of the distribution request of the stored video data 395 from the recording client 202 when the setting of the viewing limitation is changed from invalid to valid in step S372 in FIG. 3. In a manner as described above, a time period after the reception of the distribution request of the stored video data 395 and before the start of the distribution of the stored video data 395 can be shortened.

In the above-described exemplary embodiment, a case that the distribution of the video data 390 to the general client 201 and the recording client 202 is suspended according to the reception of the instruction involving the invalidation of, for example, the masking processing is exemplified. However, while the masking area is still not included in the video data 390, the video data may be distributed to the general client 201 and the recording client 202.

Similarly, for example, in a case where the viewing limitation is the panning angle of the image capturing unit 145 or the range limitation of the tilting angle, the distribution of the video data 390 is not suspended immediately upon receiving the instruction involving the invalidation of the viewing limitation but may be suspended after the control instruction beyond the range limitation of the panning angle or the tilting angle is actually received.

More specifically, when the camera server 100 receives the instruction involving the invalidation of the viewing limitation of the video and subsequently the area with the viewing limitation is included in the video data, the distribution of the video data to the client having no viewing authority for the area with the viewing limitation may be suspended. Accordingly, the continuity of the video received by the client who has no viewing authority of the area with the viewing limitation can be prevented from being degraded.

Now, processing by the recording client 202 is described below with reference to FIG. 4. The recording client 202 is a recording apparatus that receives and records video data from the server apparatus (i.e., camera server 100). The CPU 210 of the recording client 202 reads the recording program 420 stored in the second storage device 230 out to the primary storage device 220 to execute the processing thereof.

In step S400, the CPU 210 of the recording client 202 determines whether it becomes a time for making the distribution request of the video data 390 based on the setting of a recording frame rate. In a case where the recording client 202 determines that it becomes a time for making the distribution request of the video data 390 (YES in step S400), then in step S410, the recording client 202 transmits the distribution request of the video data 390 to the camera server 100 and, in step S420, resets a timer.

In a case where the recording client 202 receives the video data 390 before the timer expires (YES in step S430), then in step S440, the recording client 202 records the received video data 390 in the secondary storage device 230 and, in step S450, determines whether there is a lack of distribution of the video data 390. In step S450, the recording client 202 determines whether there is a lack in the video data 390 received from the camera server 100 based on the recording frame rate. The recording client 202 may determine that there is a lack in the video data 390, in a case where the recording client 202 receives a notification indicating that the distribution of the video data 390 from the camera server 100 is suspended. In a case where a substitute image is transmitted instead of the captured image when the distribution is suspended with respect to the general client 201 as well as in a case where the captured image with the viewing limitation is transmitted instead of the suspension of the distribution, the recording client 202 can also determine that there is a lack. In this case, the recording client 202 determines that there is a lack in a case where a notification to perform the limited processing is received from the camera server 100.

As described above, in step S420, the recording client 202 determines whether there is a limiting period in distributing the video data by the camera server 100.

In a case where the recording client 202 determines that there is a lack of the video data 390 (YES in step S450), then in step S470, the recording client 202 transmits the distribution request of the stored video data 395 to the camera server 100 to acquire the stored video data 395. On the other hand, in a case where the recording client 202 determines that there is no lack of the video data 390 (NO in step S450), the processing returns to step S400.

In a case where the recording client 202 does not receive the video data 390 before the timer expires (NO in step S430), then in step S460, the recording client 202 determines whether the camera server 100 is suspending the transmission of the video data 390. The recording client 202 of the present exemplary embodiment determines the suspension of the distribution of the video data 390 upon receiving a notification of the suspension of the distribution of the video data 390 from the camera server 100.

In a case where the recording client 202 determines that the camera server 100 is suspending the transmission of the video data 390 (YES in step S460), the processing returns to step S430 for a standby. Accordingly, the distribution request of a large amount of video data is prevented from being transmitted during the suspension of the distribution of the video data 390.

The general client 201 acquires and displays the video data based on the display program 400. More specifically, processing performed from step S400 through S430 in FIG. 4 is similar to that performed by the recording program 420. In a case where the general client 201 receives the video data 390 from the camera server 100 (YES in step S430), then in step S440, the general client 201 causes the display 260 to display the received video data, and the processing then returns to step S400.

The privileged client 200 can perform the above-described processing by using the display program 400 and the recording program 420. The privileged client 200 runs the setting change program 410 according to the operation of the setting tool and thus can acquire the privileged video data without the viewing limitation from the camera server 100.

Figure 4:
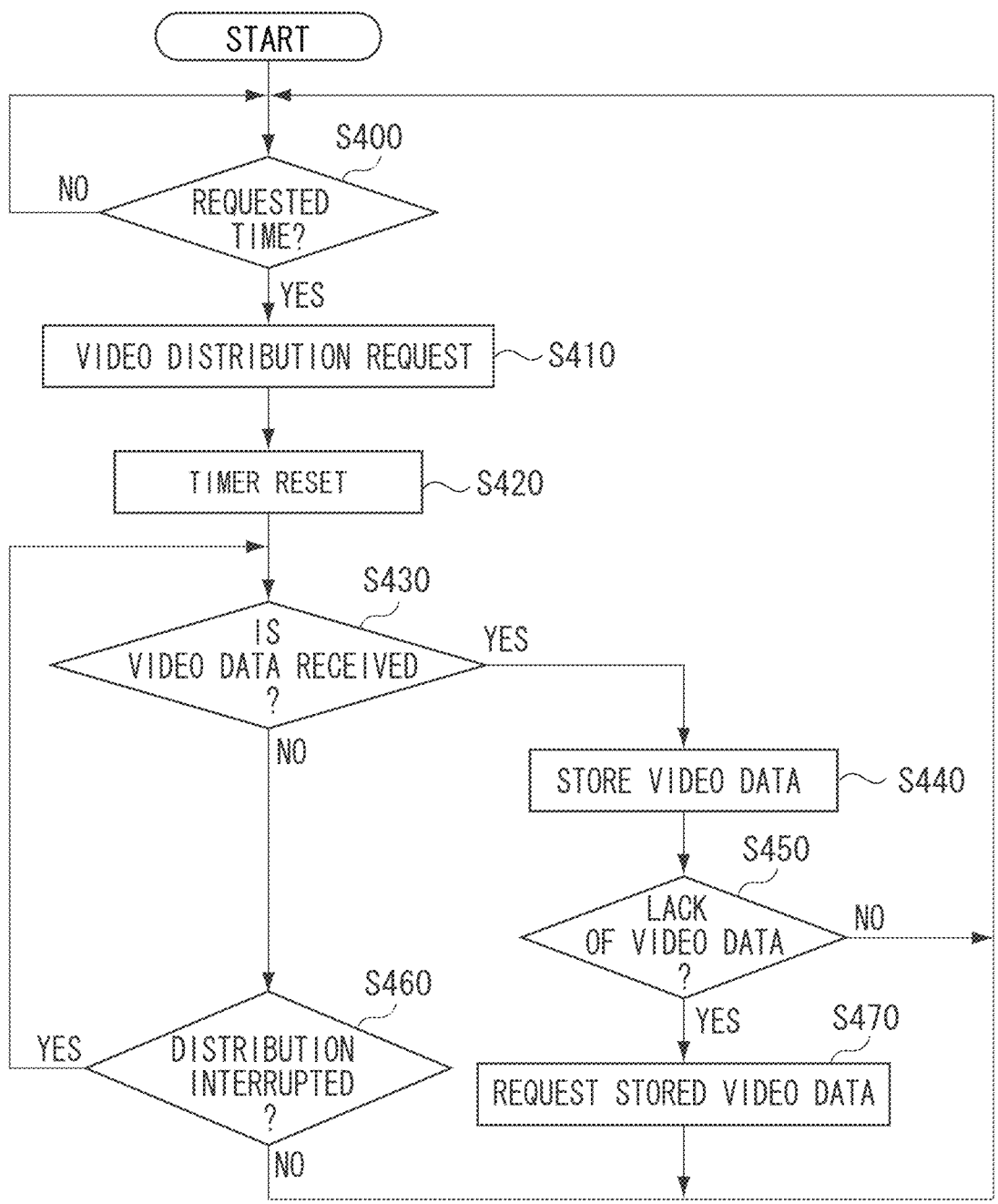
FIG. 4 is a flow chart illustrating processing performed by the client.

In step S470 in FIG. 4, the recording client 202 may acquire the stored video data 395 to which the viewing limitation is applied after the storage thereof. For example, the recording client 202 can acquire the stored video data 395 to which the masking processing is applied based on the setting after it is changed by the privileged client 200. For example, the recording client 202 can acquire only video that matches the viewing limitation or the preset limitation according to the setting after it is changed by the privileged client 200. The unmatched video may be deleted at that moment.

Accordingly, since the stored video to which the latest limiting setting is retroactively applied compensates for the lack of the recorded video, the unintended distribution and recording of the video under the privilege of an administrator who uses the setting tool can be avoided. In addition to the above, continuity of the recording video can be kept.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A network camera comprising:
   a processor; and
   a memory communicatively coupled to the processor for storing computer-executable instructions that, when executed by the processor, perform operations comprising:
      receiving an image captured by an image capturing unit;
      superimposing a privacy mask onto the captured image, the privacy mask masking a part of the captured image;
      transmitting the captured image with the privacy mask to a non-privileged client apparatus;
   in response to receiving a request from a privileged client apparatus to change a size or a position of the privacy mask onto the captured image by the privileged client apparatus,
      suspending the transmission of the captured image with the privacy mask to the non-privileged client apparatus;
      transmitting the captured image without superimposing the privacy mask onto the captured image to the privileged client apparatus in which the transmitted captured image without the privacy mask is displayed while the transmission of the captured image with the privacy mask to the non-privileged client apparatus is suspended; and
      setting a new size or position of the privacy mask based on setting data sent from the privileged client apparatus.

2. The network camera according to claim 1, wherein a request for setting an operation limitation of panning and tilting of the image capturing unit is received as another request for transmitting the captured image without superimposing the privacy mask onto the captured image.

3. A method for transmission comprising:
   receiving an image captured by an image capturing unit;
   processing a limitation of viewing of the captured image;

superimposing a privacy mask onto the captured image with the limitation to a non-privileged client apparatus, the privacy mask masking a part of the captured image;

in response to receiving a request from a privileged client apparatus to change a size or a position of the privacy mask onto the captured image by the privileged client apparatus, suspending the transmission of the captured image with the privacy mask;

transmitting the captured image without superimposing the privacy mask onto the captured image to the privileged client apparatus in which the transmitted captured image without the privacy mask is displayed while the transmission of the captured image with the privacy mask to the non-privileged client apparatus is suspended; and setting a new size or position of the privacy mask based on setting data sent from the privileged client.

4. The method according to claim 3, wherein a request for setting an operation limitation of panning and tilting of the image capturing unit is received as another request for transmitting the captured image without superimposing the privacy mask onto the captured image.

5. A non-transitory computer-readable medium storing computer-executable instructions that, when executed by a computer, perform a method for transmission comprising:

receiving an image captured by an image capturing unit;

superimposing a privacy mask onto the captured image, the privacy mask masking a part of the captured image;

transmitting the captured image with the privacy mask to a non-privileged client apparatus;

in response to receiving a request from a privileged client apparatus to change a size or a position of the privacy mask onto the captured image by the privileged client apparatus, suspending the transmission of the captured image with the privacy mask to the non-privileged client apparatus;

transmitting the captured image without superimposing the privacy mask onto the captured image to the privileged client apparatus in which the transmitted captured image without the privacy mask is displayed while the transmission of the captured image with the privacy mask to the non-privileged client apparatus is suspended; and setting a new size or position of the privacy mask based on setting data sent from the privileged client apparatus.

6. The method according to claim 5, wherein a request for setting an operation limitation of panning and tilting of the image capturing unit is received as another request for transmitting the captured image without superimposing the privacy mask onto the captured image.

* * * * *